United States Patent [19]

Cerise et al.

[11] Patent Number: 4,495,039
[45] Date of Patent: Jan. 22, 1985

[54] METHOD FOR ACTIVATING A PYROCARBON ELECTRODE TIP

[75] Inventors: Osvaldo Cerise, Doues; Pietro Arru; Franco Vallana, both of Turin, all of Italy

[73] Assignee: Sorin Biomedica S.p.A., Saluggia, Italy

[21] Appl. No.: 405,784

[22] Filed: Aug. 6, 1982

[30] Foreign Application Priority Data

Aug. 7, 1981 [IT] Italy ............... 68103 A/81

[51] Int. Cl.³ ............................. C25B 11/12
[52] U.S. Cl. ................... 204/130; 128/784; 128/419 P
[58] Field of Search ............ 204/130, 56 R, 294; 128/419 P, 484, 485, 486, 784, 785, 786; 252/425.3, 444; 423/441, 442, 445, 460, 481

[56] References Cited

U.S. PATENT DOCUMENTS 3,671,411 6/1972 Ray et al. ................... 204/130
4,281,668 8/1981 Richter et al. ............... 128/419 P X

FOREIGN PATENT DOCUMENTS 7240119 10/1972 Japan ...................... 204/130
4020720 5/1974 Japan ...................... 204/130
1257022 12/1971 United Kingdom ......... 204/130

Primary Examiner—G. L. Kaplan
Assistant Examiner—Nam X. Nguyen
Attorney, Agent, or Firm—Sughrue, Mion, Zinn, Macpeak and Seas

[57] ABSTRACT

A pyrocarbon tip for a cardiac stimulator electrode is subjected to an anodic electrolytic treatment in which a strong, concentrated acid with oxidizing properties, or a mixture of two or more such acids, is used as the electrolyte. The treatment is carried out with a voltage greater than 1 V, preferably between 1 and 20 V, and with a current density greater than 3 mA/mm², preferably between 30 and 40 mA/mm². Pyrocarbon tips treated in this manner have very low bias voltages in use.

4 Claims, 5 Drawing Figures

METHOD FOR ACTIVATING A PYROCARBON ELECTRODE TIP

BACKGROUND OF THE INVENTION

The present invention relates to electrodes used in cardiac stimulators.

One of the materials which is best suited for the manufacture of electrode tips for cardiac stimulators (that is the portion of the electrode which will come into contact with the cardiac wall) is pyrocarbon (or pyrolytic carbon).

This material, either pure or with the addition of small percentages of silicon, has indeed excellent characteristics of biocompatability, mechanical strength and lack of variation with time.

However, an electrode for cardiac stimulators having a tip of pyrocarbon would give rise to high bias voltages in use (that is a high residual electrical potential on the tip at the instant at which the stimulation current returns to zero after a stimulation pulse of the myocardium), which would give rise to a power loss in the cardiac stimulation operation.

The present invention has the object of forming a tip of "activated" pyrocarbon, that is free from the said disadvantage and hence usable to advantage as an electrode tip for a cardiac stimulator.

SUMMARY OF THE INVENTION

In order to achieve this object the present invention provides a method for activating a pyrocarbon tip for cardiac stimulators, the characteristic of which lies in the fact that it consists of subjecting the tip to an anodic electrolytic treatment in which at least one strong, concentrated acid with oxidizing properties is used as the electrolyte, the electrolytic treatment being effected with a voltage greater than 1 V and with a current density greater than 3 mA/mm$^2$.

BRIEF DESCRIPTION OF THE DRAWINGS

Further characteristics and advantages of the present invention will emerge from the detailed description which follows with reference to the appended drawings, in which.

DETAILED DESCRIPTION OF THE INVENTION

Figure 1:
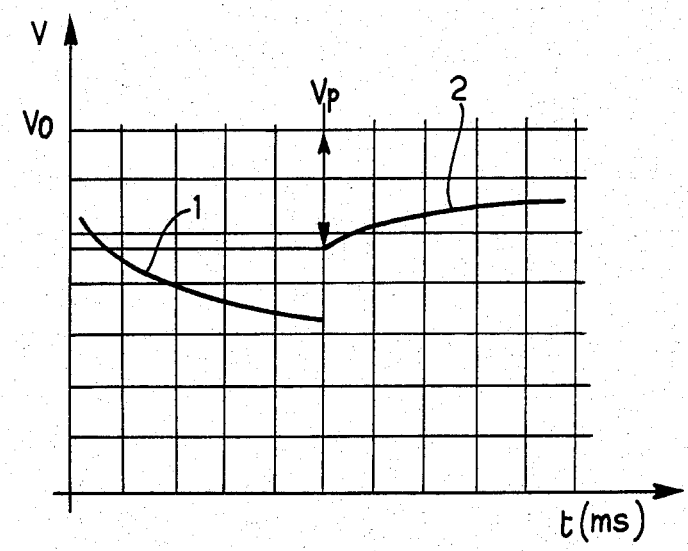
FIG. 1 is a graph illustrating the phenomenon of polarization of an electrode for a cardiac stimulator having a pyrocarbon tip.

The graph of FIG. 1 illustrates the changes in voltage when an electrode with a pyrocarbon tip immersed in a solution of Tyrode, which simulates the characteristics of human plasma, is subjected to a current pulse with a constant strength of 2.5 mA for a period of 0.5 ms.

The plot 1 illustrates the changes in the voltage (negative) during the pulse and the plot 2 illustrates the changes in the voltage after the impulse has ceased.

$V_P$ shows the bias voltage, that is the residual voltage at the instant at which the pulse ceases.

From an examination of the graph, it is clearly seen that the residual voltage is substantial, whereby the use of an electrode with such a pyrocarbon tip in a cardiac stimulator would give rise to a power loss in operation.

According to the present invention, the pyrocarbon tip of the electrode used to plot the graph of FIG. 1 is subjected to an electrolytic activation treatment.

The pyrocarbon tip has been used as the anode in an electrolytic cell with a pyrocarbon cathode and an electrolyte constituted by a mixture of fifty parts by weight of concentrated sulphuric acid (98% by weight) and fifty parts by weight of concentrated nitric acid (65% by weight).

The treatment was carried out for 20 seconds with a voltage of 5 V and a current density at the anode of 20 mA/mm$^2$.

The pyrocarbon tip of the electrode used to plot the graph of FIG. 1 was replaced by the pyrocarbon tip activated electrolytically in the manner described above.

Figure 2:
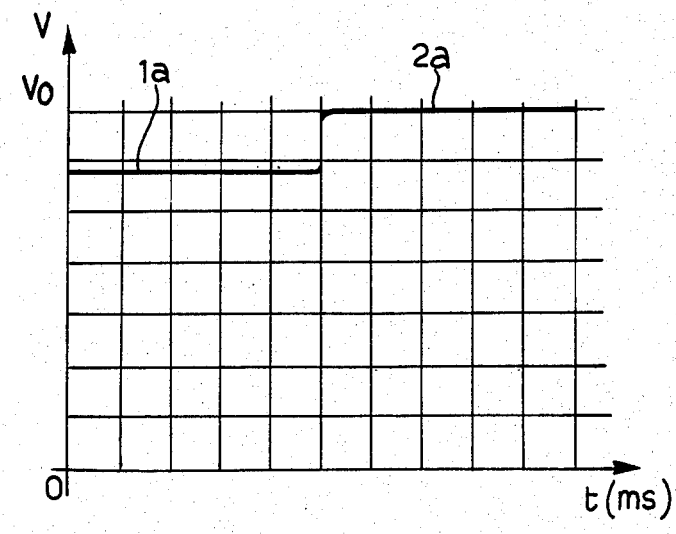
FIG. 2 is a graph similar to that of FIG. 1 relating to the same electrode in which the tip has been replaced by a pyrocarbon tip activated by the method of the invention.

The graph of FIG. 2 illustrates the changes in the voltage in this electrode under the same conditions as in the graph of FIG. 1.

The plot 1a illustrates the changes in the voltage during the pulse and the plot 2a shows the changes in the voltage after the pulse has ceased.

From a comparison of the plots 1a, 2a of FIG. 2 and the corresponding plots 1, 2 of FIG. 1, it is clear that the electrode with the tip activated according to the invention effectively does not polarize during the pulse and hence the bias voltage is practically zero.

Tests carried out by the applicant have enabled the fact to be ascertained that the phenomenon of the disappearance of the bias voltage occurs when a pyrocarbon tip for an electrode for cardiac stimulators is subjected to an anodic electrolytic treatment with the use of a strong, concentrated acid with oxidizing properties, such as for example sulphuric acid, nitric acid, perchloric acid and phosphoric acid in concentrated solutions or a mixture of two or more of these acids, as the electrolyte.

The cathode (counter-electrode) is preferably constituted by pyrocarbon; it is, however, possible to use cathodes of other materials which are resistant to the corrosive action of the electrolyte.

The voltage may vary from 1 to 20 volts and the current density may be between 3 and 40 mA/mm$^2$.

The electrolytic treatment time may vary between 5 and 45 seconds and the voltage depends on the geometrical characteristics of the electrode, the cathode, and of the electrolytic cell.

Figure 3:
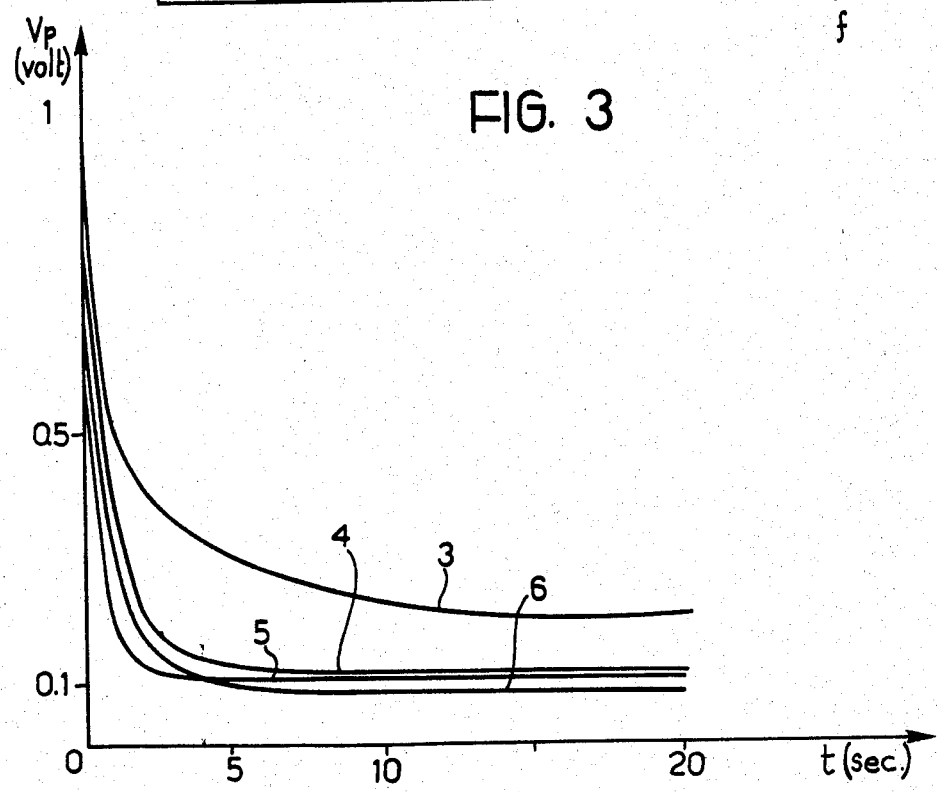
FIG. 3 is a graph illustrating the variations in the bias voltage as a function of the duration of the electrolytic treatment according to the invention.

The graph of FIG. 3 illustrates the variation in the bias voltage $V_P$ of a pyrocarbon tip at a constant voltage of 5 V in various concentrated acid solutions as a function of the electrolytic treatment time.

Figure 4:
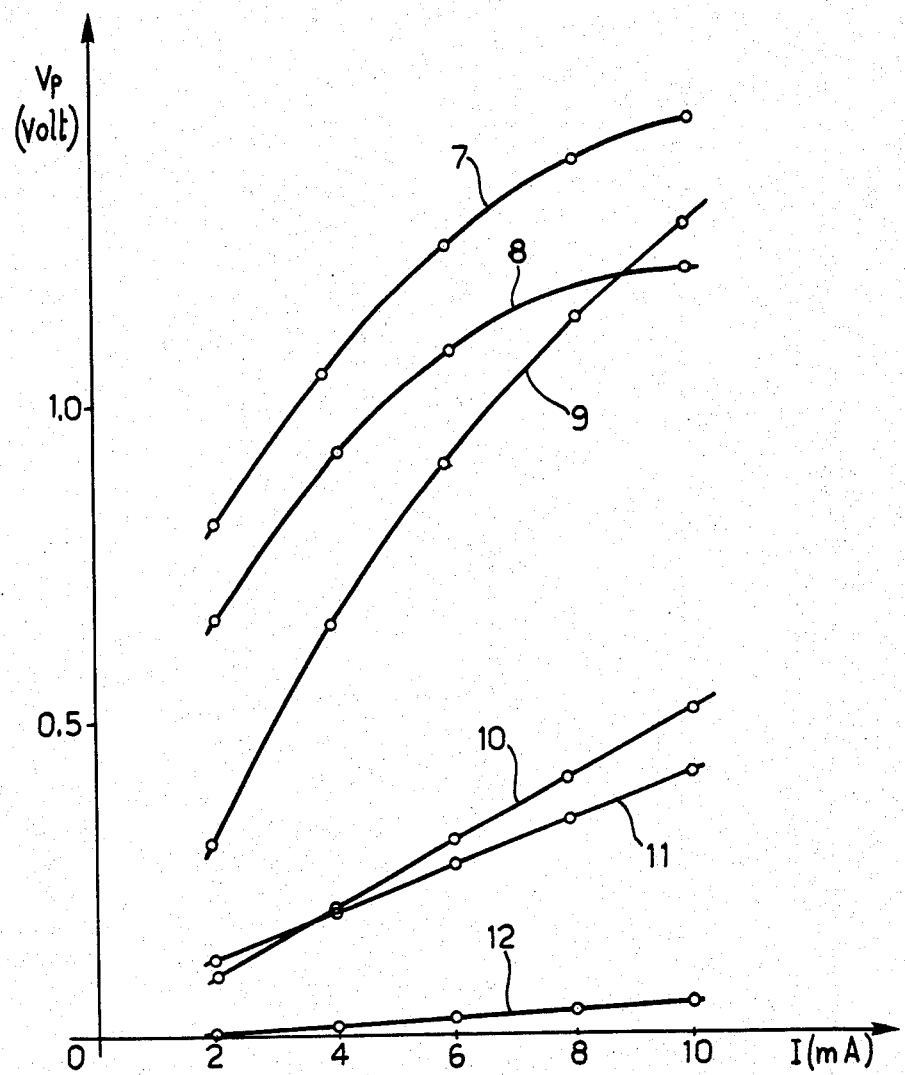
FIG. 4 is a graph illustrating the variation in the bias voltage as a function of the current strength of the cardiac stimulation pulse.

Plot 3 relates to a tip treated electrolytically in a solution of 85% concentrated phosphoric acid and plots 4, 5 and 6 relate to tips treated electrolytically in respective solution of 65% concentrated nitric acid, 70% concentrated perchloric acid and 98% concentrated sulphuric acid. The graph of FIG. 4 illustrates the variation in the bias voltages on variation of the current strength of the cardiac stimulation pulse between 2 and 10 mA for various types of electrodes with tips of different materials.

The bias voltages were corrected to take account of the polarization of the cathode.

Plot 7 illustrates the variation in the bias voltage of an electrode with an un-treated pyrocarbon tip.

Plot 8 relates to an electrode with a 90/10 platinum/iridium tip, plot 9 relates to an electrode with a tip constituted by a bundle of platinum wires in a platinum mesh, plot 10 relates to an electrode with a glassycarbon tip, plot 11 relates to an electrode with a porous platinum tip and plot 12 relates to an electrode with a pyrocarbon tip treated by the method according to the present invention.

From a comparison of the various curves it is clear that the electrode with the pyrocarbon tip treated according to the invention represents a substantial improvement over the known art.

A further advantage of the present invention lies in the fact that the impedance of an electrode with a pyrocarbon tip activated by the method of the invention is substantially lower than that of the electrodes with platinum/iridium tips and porous platinum tips.

Figure 5:
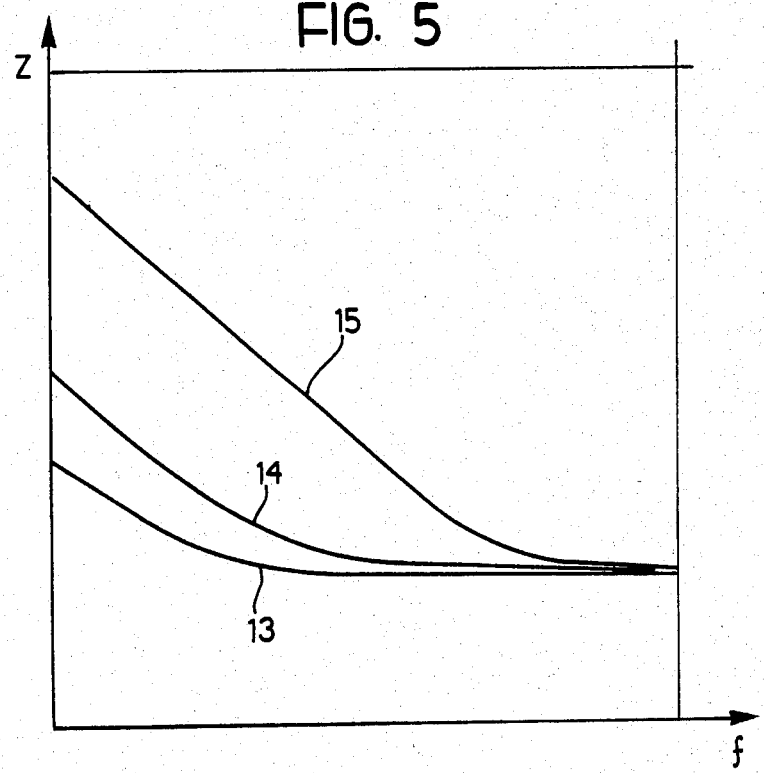
FIG. 5 is a graph illustrating the variation in the impedance of various types of electrode tips as a function of the sine wave frequency applied thereto.

The graph of FIG. 5 illustrates the variation in the impedance Z as a function of the sine wave frequency F applied to the electrode.

The values of the impedance relating to an electrode with an activated pyrocarbon tip according to the invention are given in plot 13. These are lower, for every frequency considered, than those of an electrode with a porous platinum tip (plot 14) and those of an electrode with a 90/10 platinum/iridium tip (plot 15), measured under the same experimental conditions.

Naturally, the principle of the invention remaining the same, the manner of execution of the activation treatment can be varied widely with respect to that described by way of example without thereby departing from the scope of the present invention.

What is claimed is:

1. Method for activating a pyrocarbon tip for an electrode for a cardiac stimulator, consisting of subjecting the tip to an anodic electrolytic treatment in an electrolyte composed of a mixture of 50 parts by weight of concentrated sulphuric acid (98% by weight) and 50 parts by weight of concentrated nitric acid (65% by weight), said electrolytic treatment being carried out with a voltage greater than 1 V and a current density greater than 3 mA/mm$^2$.

2. Method as claimed in claim 1, wherein said voltage is between 2 and 20 V and said current density is between 3 and 40 mA/mm$^2$.

3. Method as claimed in claim 1, wherein said electrolytic treatment is carried out for a period of between 5 and 45 seconds.

4. Method as claimed in claim 1, wherein said electrolyte is selected from the group consisting of nitric acid, sulphuric acid, percholoric acid and phosphoric acid and their mixtures.

* * * * *